United States Patent [19]

Sepetka et al.

[11] Patent Number: 5,308,342
[45] Date of Patent: May 3, 1994

[54] VARIABLE STIFFNESS CATHETER

[75] Inventors: Ivan Sepetka, Redwood City; Phong Pham, San Jose; Erik T. Engelson, Portola Valley, all of Calif.

[73] Assignee: Target Therapeutics, Inc., Fremont, Calif.

[21] Appl. No.: 741,775

[22] Filed: Aug. 7, 1991

[51] Int. Cl.⁵ ............................................. A61M 25/00
[52] U.S. Cl. ..................................... 604/282; 604/264; 604/280
[58] Field of Search .................. 604/264, 280–282, 604/96; 128/656–658, 772; 606/194

[56] References Cited

U.S. PATENT DOCUMENTS

| | | | |
|---|---|---|---|
| 4,282,876 | 8/1981 | Flynn | 604/280 |
| 4,531,943 | 7/1985 | Van Tassel et al. | 604/280 |
| 4,573,476 | 3/1986 | Ruiz | 604/280 |
| 4,596,563 | 6/1986 | Pande | 604/280 |
| 4,636,346 | 1/1987 | Gold et al. | 604/280 |
| 4,690,175 | 9/1987 | Ouchi et al. | 604/282 |
| 4,739,768 | 4/1988 | Engelson . | |
| 4,775,371 | 10/1988 | Mueller, Jr. | 604/280 |
| 4,846,814 | 7/1989 | Ruiz | 604/281 |
| 4,863,442 | 9/1989 | De Mello et al. | 604/282 |
| 4,898,591 | 2/1990 | Jang et al. | 604/282 |
| 4,899,787 | 2/1990 | Ouchi et al. | 604/282 |
| 4,961,731 | 10/1990 | Bodicky et al. | 604/280 |
| 5,069,662 | 12/1991 | Bodden | 604/101 |
| 5,078,702 | 1/1992 | Pomeranz | 604/282 |
| 5,085,649 | 2/1992 | Flynn | 604/282 |

Primary Examiner—C. Fred Rosenbaum
Assistant Examiner—Mark Bockelman
Attorney, Agent, or Firm—Morrison & Foerster

[57] ABSTRACT

A catheter composed of an outer coaxial tube or relatively high flexibility and three tandemly disposed inner coaxial tube segments that vary in stiffness with the stiffest being located at the proximal end of the catheter and the least stiff ending proximal of the proximal end of the catheter. The catheter thus has four regions of different stiffness/flexibility.

9 Claims, 3 Drawing Sheets

VARIABLE STIFFNESS CATHETER

DESCRIPTION

1. Technical Field

This invention is in the general field of surgical devices and relates specifically to an improved catheter tube structure that may be used with a guide wire to access target sites through tortuous, small diameter vessels with less likelihood of kinking or other malfunction.

2. Background

Catheters are hollow tubes that are inserted through the vasculature or other internal body passageways to access a particular internal body site for various diagnostic or therapeutic purposes. Angiography catheters are used to deliver radiopaque agents to a target site to enable radiographic visualization of the site. In the treatment of localized diseases such as solid tumors, they are used to administer chemotherapeutic agents or vasoocclusive agents. Catheters are similarly used to deliver vasoocclusive devices (e.g., coils) to sites of aneurysm. Inflatable catheters often referred to as balloon catheters, are used to dilate vessels.

For insertion through tortuous, small vessels such as those found in the peripheral vasculature or organs such as the brain and liver, catheters are commonly used in combination with a flexible torqueable guide wire. In this procedure, the guide wire is advanced through the vessel and the catheter is threaded over the guide wire. At tortuous sites in the vessel, the assembly is advanced by alternately guiding the wire through the site and then threading the catheter over the advanced segment of the wire. In order to be useful in such applications, the catheter must meet demanding physical requirements so that it does not become locked against the guide wire or become kinked as it is passed through particularly tortuous segments of the vessel. In this regard, commonly owned U.S. Pat. No. 4,739,768 describes a catheter structure specifically designed to overcome problems associated with accessing tortuous, small vessels.

The specific catheter embodiment shown in U.S. Pat. No. 4,739,768 consists of a coaxial assembly of two tubes, one of which is relatively long and stiff and defines a proximal portion of the catheter and the other of which is relatively short and flexible and defines the distal end of the catheter. The flexible distal end allows the catheter to be advanced axially over sharper and/or more frequent wire bends with less likelihood of malfunction. The patent mentions (col. 5) that for longer tortuous paths the catheter may include one or more intermediate segments having flexibilities intermediate those of the proximal and distal portions of the catheter and which, together with the distal portion, constitute 10% to 40% of the catheter length. The stated purpose of such intermediate sections is to provide greater column strength than the distal portion of the two-section embodiment and greater flexibility than the proximal section of that embodiment. The patent does not provide any specific examples of such multi-segment catheters or indicate any other purposes of a multi-segment structure.

The present invention relates to a catheter which has four segments of different flexibility. This novel structure improves on the performance and durability of the two-segment structure depicted in U.S. Pat. No. 4,739,768.

DISCLOSURE OF THE INVENTION

The invention is a catheter for use in combination with a guide wire for placement within a tortuous, small vessel, said catheter comprising an elongate tubular body having proximal and distal ends and a lumen extending between said ends for receiving the guide wire, said body comprising:

(a) an outer coaxial tube extending continuously between said ends, having a wall thickness of 0.05 to 0.13 mm and being made of a polymer having a flexural modulus of about 100,000 to 250,000 Kpa and (b) proximal, intermediate, and distal inner coaxial polymeric tube segments positioned contiguously in tandem within the outer tube from said proximal end to a site proximal said distal end, the proximal segment having a wall thickness of 0.08 to 0.18 mm and being made of a polymer having a flexural modulus of about 1,500,000 to 1,800,000 kpa, the intermediate segment being less stiff than the proximal segment and the distal segment being less stiff than the intermediate segment but stiffer than the portion of the outer tube extending from said site to said distal end.

DETAILED DESCRIPTION OF THE INVENTION

Figure 1:
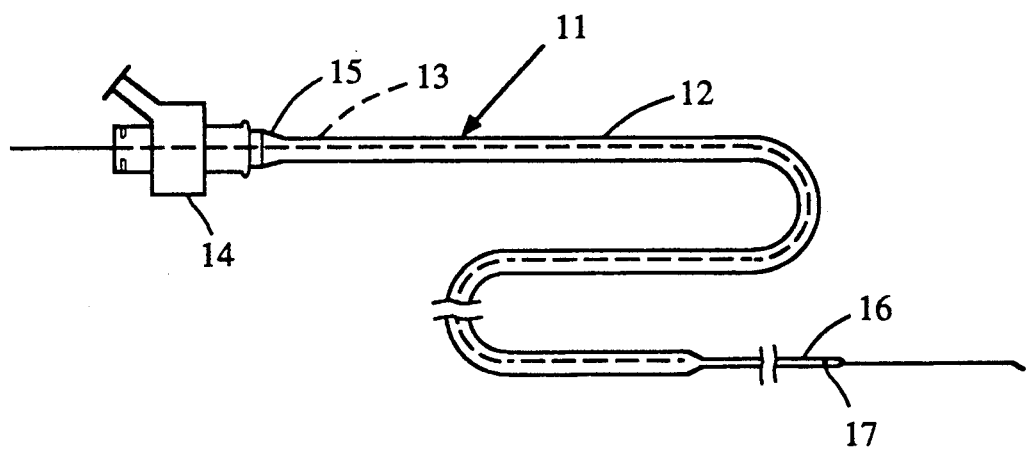
FIG. 1 is an elevational view of a catheter assembly showing the catheter of the invention in combination with a guide wire.

FIG. 1 is a general view showing a catheter assembly, generally designated 11, that includes the inventive catheter 12 in combination with a guide wire 13. The details of the catheter construction that distinguish it from prior structures are not shown in FIG. 1. The assembly includes a standard fitting 14 through which the guide wire is received and to which the proximal end 15 of the catheter is removably attached. As depicted, the catheter is a continuous tubular body that extends from proximal end 15 to distal end 16 and through which the guide wire extends. The distal end of the guide wire extends outwardly of the distal end 16 of the catheter. The distal region of the catheter typically carries one or more radiopaque bands 17 so that the location of the distal region of the catheter within the vessel may be visualized radiographically.

Figure 2:
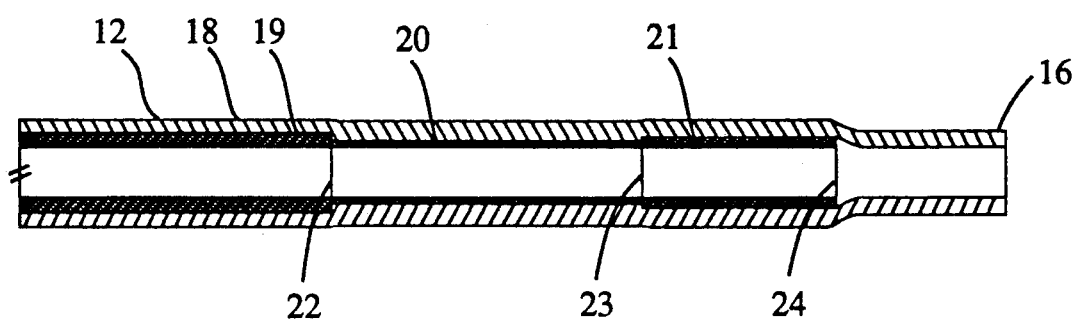
FIG. 2 is an enlarged sectional view of a portion of the catheter of the invention showing the coaxial segmented structure of the catheter.

Details of the structure of catheter 12 are depicted in FIG. 2. It is composed of an outer tube 18 and three inner coaxial tubular segments 19, 20, 21. As shown, the three inner coaxial tubular segments are disposed in tandem within the outer tube and are contiguous to each other (i.e., their respective ends abut each other). The outer tube 18 extends continuously over the entire length of the catheter, which typically will be over 50 to 210 cm, more usually 80 to 150 cm. The outer diameter of tube 18 (as measured at proximal end 15) will normally be 0.75 to 2.00 mm, preferably 0.85 to 1.30 mm. As seen in FIG. 2, the outer tube may neck down at its distal end and its outer diameter at the distal end may be slightly smaller than at its proximal end. The outer tube will normally have a wall thickness of about 0.08 to 0.16 mm, preferably about 0.10 to 0.13 mm. It is made from a polymer having a flexural modulus (as measured by ASTM D-790) of about 100,000 to 250,000 kpa, such as low density polyethylene.

The proximal inner tubular segment 19 extends from the proximal end 15 of the catheter to junction 22. This distance will normally be 10 to 70 cm, more usually 40 to 60 cm, and preferably about 50 cm. Its wall thickness is about 0.08 to 0.18 mm, preferably about 0.10 to 0.13 mm, and it is made of a polymer having a flexural modulus of about 1,500,000 to 1,800,000 kpa such as polypropylene. The portion of the catheter from proximal end 15 to junction 22 is thus the stiffest portion of the catheter. The inner diameter of segment 19 will normally be 0.45 to 0.75 mm.

Intermediate inner tubular segment 20 extends from the distal end of segment 19 (junction 22) to junction 23. That distance will normally be 30 to 100 cm, more normally 70 to 90 cm, preferably about 80 cm. This segment is less stiff than segment 19. Accordingly, its wall thickness is less than segment 19 and/or it is made of a polymer with a lower flexural modulus than the polymer forming segment 19. In a preferred embodiment, it is made of the same polymer and has a smaller wall thickness, normally 0.05 to 0.13 mm, more usually 0.05 to 0.08 mm. In the preferred embodiments segments 19 and 20 may be made of a continuous length of tubing having an appropriately tapered outer diameter.

The third distal segment 21 extends from the distal end of segment 20 (junction 23) to a site 24 proximal of the distal end of the catheter. The distance from junction 23 to site 24 will usually be 5 to 20 cm, more usually 7 to 15 cm, preferably about 10 cm.

Corresponding, the distance from site 24 to the distal end 16 of the catheter will usually be 5 to 20 cm, more usually 7 to 15 cm, and preferably about 10 cm. The distance from junction 22 to the distal end of the catheter will be greater than about 50% of the entire length of catheter 12, more usually greater than about 60% of the entire catheter length. Segment 21 is less stiff than segment 20 and provides a transition in flexibility between segment 20 and the portion of outer tube 18 that extends beyond site 24. It follows that the wall thickness of segment 21 is less than that of segment 20 and/or it is made from a polymer having a lower flexural modulus than the polymer forming segment 20. In this regard, it is preferable that segment 21 be made of a polymer having a significantly lower flexural modulus than the polymer forming segment 20 but higher than that of the polymer from which the outer tube 18 is made. The distal segment 21, for instance, may be linear, low density polyethylene. Typically, the flexural modulus of the polymer forming segment 21 will be 150,000 to 350,000 kpa, more usually 200,000 to 300,000 kpa. The wall thickness of segment 21 will normally be 0.05 to 0.10 mm, preferably 0.06 to 0.09 mm. The inner diameters of segments 20 and 21 are preferably substantially the same as that of segment 19.

Although the joints 22 and 23 are depicted as butt joints in the drawings, these joints may be overlap joints.

The invention catheter thus has four segments of different flexibility/stiffness and becomes increasingly flexible from segment-to-segment distally. The axial flexibility/stiffness gradient of the invention catheter is thus more gradual than in the two-segment embodiment of U.S. Pat. No. 4,739,768 and the change in flexibility stiffness between segments is not as great as in said two-segment embodiment. In particular, the inclusion of segment 21 allows the distal end of the catheter to be tracked around sharp bends with less likelihood of kinking occurring at the transition between the outer tube and the distal end of the inner coaxial tubing. This difference is shown in FIGS. 3A and 3B.

Figure 3A:
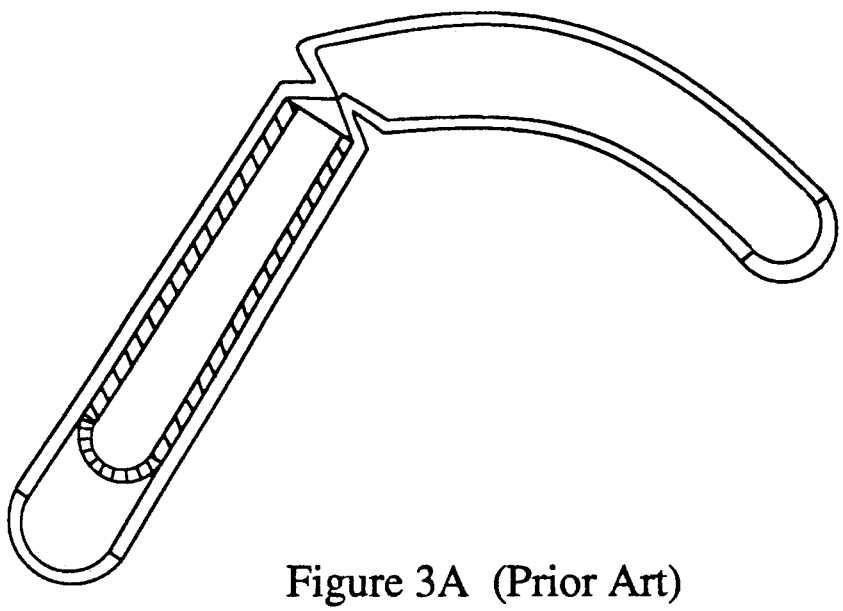
FIGS. 3A and 3B are sectional schematic views which show how the prior art structure (3A) may perform at a sharp bend as compared to the invention structure (3B).

FIG. 3A represents the prior art structure in which there was a greater change in flexibility/stiffness at the transition between the coaxial tube portion of the catheter and the single tube distal end. When the region was tracked through a sharp bend, kinking could occur at the transition. Such kinking hinders the insertion (tracking) procedure and may lead to structural failure (delamination, separation) at the transition.

Figure 3B:
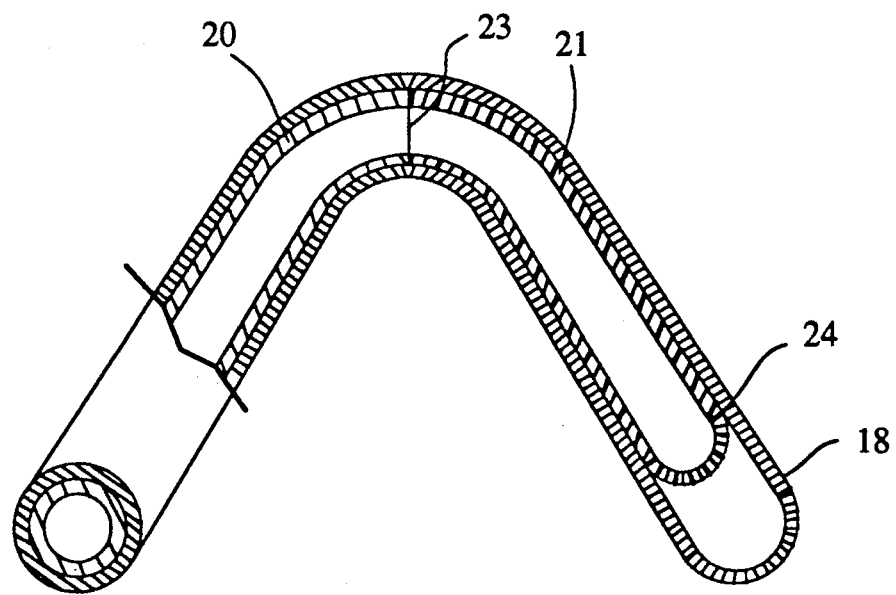

FIG. 3B represents the invention structure in which the transition in flexibility/stiffness between the coaxial tube portion of the catheter and the single tube distal end is lessened. Such structure improves the trackability of the catheter through sharp bends (less likelihood of kinking) and reduces the likelihood of fatigue stress failure, delamination, or other structural failure at that transition.

Aside from its improved performance and durability, the invention catheter operates in the same manner as the catheter described in U.S. Pat. No. 4,739,768. Similarly, it may be constructed using the same basic techniques as are set forth in U.S. Pat. No. 4,739,768. In view of this, detailed descriptions of the manufacture and operation of the invention catheter are not required herein.

Modifications of the above-described embodiments of the catheter that are obvious to those of skill in the fields of catheter design and manufacture, materials science, and related fields are intended to be within the scope of the following claims.

We claim:

1. A catheter for use in combination with a guide wire for placement within a tortuous, small vessel, said catheter comprising an elongate tubular body having proximal and distal ends and a lumen extending between said ends for receiving the guide wire, said body comprising;
   (a) an outer coaxial tube extending continuously between said ends, having a wall thickness of 0.05 to 0.13 mm and being made of a polymer having a flexural modulus of about 100,000 to 250,000 kpa; and
   (b) proximal, intermediate, and distal inner coaxial polymeric tube segments contiguously abutted in tandem within the outer tube from said proximal end to a site proximal said distal end and which form the catheter lumen within these segments, the proximal segment having a constant wall thickness of 0.08 to 0.18 mm and being made of a polymer having a flexural modulus of about 1,500,000 to 1,800,000 kpa, the intermediate segment being less stiff than the proximal segment and the distal segment having a constant wall thickness of 0.05 to 0.10 mm and different than that of the proximal segment and being made of a polymer having a flexural modulus of about 200,000 to 300,000 kpa and being less stiff than the intermediate segment but stiffer than the portion of the outer tube extending from said site to said distal end.

2. The catheter of claim 1, wherein 1 wherein the proximal and intermediate segments are made of the same polymer and the wall thickness of the intermediate segment is less than the wall thickness of the proximal segment.

3. The catheter of claim 2, wherein the wall thickness of the intermediate segment is less than that of the proximal segment and is 0.05 to 0.13 mm.

4. The catheter of claim 3, wherein the distal segment has a wall thickness of less than that of the intermediate segment and is 0.06 to 0.11 mm.

5. The catheter of claim 1, wherein the outer diameter of the outer coaxial tube is 0.75 to 2.00 mm at the proximal end and of a smaller diameter at the distal end.

6. The catheter of claim 5 wherein the length of the outer tube is 50 to 210 cm, the length of the proximal segment is 10 to 70 cm, the length of the intermediate segment is 30 to 100 cm, and the length of the distal segment is 5 to 20 cm.

7. The catheter of claim 1 wherein the distance from the distal end of the proximal segment to the distal end of the catheter constitutes greater than 50% of the length of the catheter.

8. The catheter of claim 1 wherein the distance from the distal end of the proximal segment to the distal end of the catheter constitutes greater than 60% of the length of the catheter.

9. The catheter of claim 1 wherein the outer tube is made of low density polyethylene, the proximal and intermediate segments are made of polypropylene, and the distal segment is made of linear low density polyethylene.

* * * * *